United States Patent [19]
Shigemitsu et al.

[11] Patent Number: 4,953,228
[45] Date of Patent: Aug. 28, 1990

[54] APPARATUS FOR DETECTING PATTERN OF CREST LINE

[75] Inventors: Mineo Shigemitsu; Ryoi Onda, both of Mitaka; Toshi Minami; Osamu Nakamura, both of Tokyo, all of Japan

[73] Assignee: Secom Co., Ltd., Tokyo, Japan

[21] Appl. No.: 202,282

[22] Filed: Jun. 3, 1988

[30] Foreign Application Priority Data

Jun. 11, 1987 [JP] Japan ............................. 62-144012

[51] Int. Cl.$^5$ ............................................. G06K 9/00
[52] U.S. Cl. ......................................... 382/22; 382/4; 382/68
[58] Field of Search ................. 382/20, 21, 48, 19, 382/20, 25, 22, 4, 5, 68

[56] References Cited

U.S. PATENT DOCUMENTS

| | | | |
|---|---|---|---|
| 3,624,606 | 11/1971 | LeFevre | 382/21 |
| 3,979,722 | 9/1976 | Sakoe | 382/21 |
| 3,993,888 | 11/1976 | Fellman | 382/68 |
| 4,468,807 | 8/1984 | Moulton | 382/21 |
| 4,524,454 | 6/1985 | Ejiri | 382/21 |
| 4,710,964 | 12/1987 | Yamaguchi et al. | 382/21 |
| 4,827,527 | 5/1989 | Morita et al. | 382/4 |

Primary Examiner—Leo H. Boudreau
Attorney, Agent, or Firm—Armstrong, Nikaido, Marmelstein, Kubovcik & Murray

[57] ABSTRACT

In an apparatus for detecting a pattern of crest lines according to the present invention, an object area to be treated is mechanically divided into a plurality of picture elements (Ej), and the direction of crest lines such as a dactylogram can be easily detected by a simple calculation consisting of addition, subtraction, multiplication, and division, by using evaluated shading values in a series (Si) of picture elements, each unit area (UA) consisting of some picture elements of all picture elements in the object area. Therefore, even when the crest lines are cut off, crushed, or branched off, on the way thereof, the direction of the crest lines can be correctly detected.

4 Claims, 5 Drawing Sheets

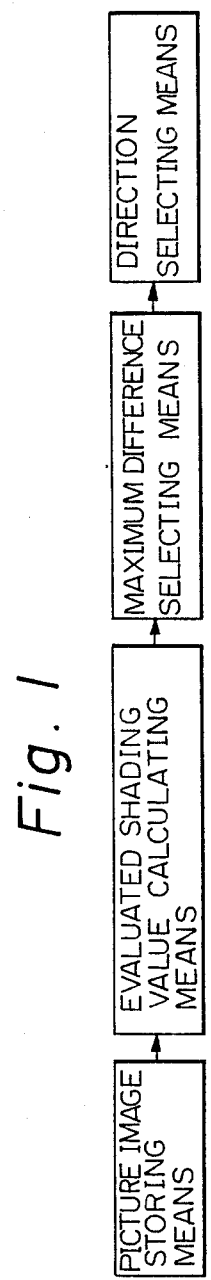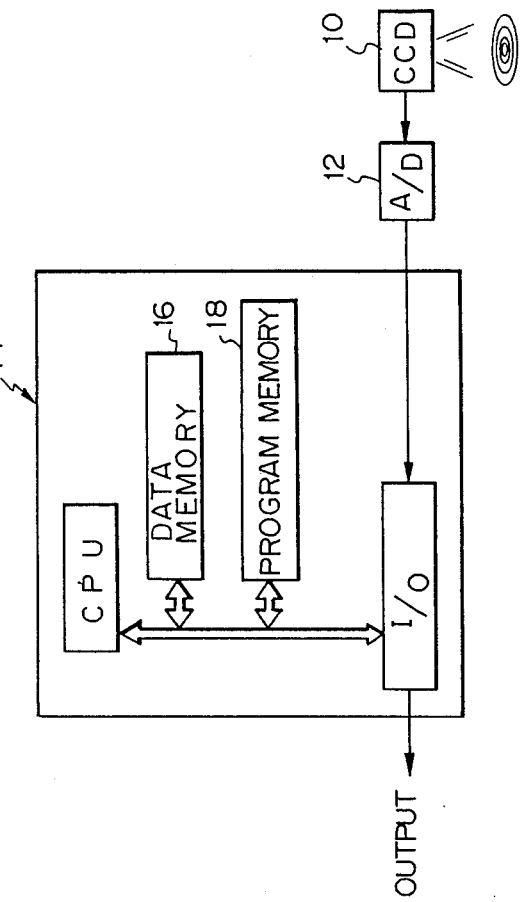

APPARATUS FOR DETECTING PATTERN OF CREST LINE

BACKGROUND OF THE INVENTION

1. Field of the Invention

The present invention relates to an apparatus for detecting a pattern of crest lines, which apparatus is used in discriminating, for example, a dactylogram having an individual pattern of crest lines.

2. Description of the Related Art

Various apparatuses for discriminating a pattern of crest lines which is a stripe pattern consisting of a plurality of crest lines, such as a dactylogram, have been proposed. For example, an apparatus for detecting a stripe pattern is disclosed in Japanese Examined Patent Publication (Kokoku) No. 59-27945. According to the invention disclosed in the above publication, one picture element is first arbitrarily selected, which element is one of a plurality of minimum unit picture elements by which a picture image of a stripe pattern is constructed. Next, the degree of shading of each picture element is detected by a turn in one direction, which is one of a group of predetermined radial directions having the above-mentioned selected picture element as a center, and the absolute values of a shading difference between adjacent picture elements are accumulated. The same process as above-mentioned is repeated in other directions, and the direction which corresponds to the extremity of a group of the before-mentioned accumulated value, which value corresponds to each direction, is determined to be the direction of a line element of a crest line in the selected picture element. The same process as before-mentioned is repeated for each of the other picture elements.

Nevertheless, in the above-mentioned detecting system, a problem arises in that the direction of a crest line cannot be detected, or cannot be easily detected, if the crest line is cut off, crushed, or branched off, on the way thereof, such as a picture image of a dactylogram.

SUMMARY OF THE INVENTION

An object of the present invention is to provide an apparatus for easily detecting the direction of crest lines of a pattern of crest lines, even when the pattern has a cut off portion, a crushed portion, or a branched off portion.

The present invention provides an apparatus for detecting a pattern of crest lines, which pattern is divided into a plurality of picture elements on a picture image thereof, each picture element having a shading value, each value being one of a predetermined number of values, comprising: means for storing each shading value in correspondence to each picture element having a shading value, in order; means for calculating a first group of evaluated values for each direction of a plurality of predetermined directions in a unit area consisting of a group of picture elements, each of which is adjacent to another, each of said first group of evaluated valves being an evaluated shading value in each series of picture elements along one direction of said plurality of predetermined directions; means for selecting a second group of values, each value being a largest difference in said first group of evaluated values for each direction; and means for selecting a direction corresponding to a maximum value in said second group of values, thereby determining a direction of crest lines of a pattern of crest lines in a unit area.

Generally, the specific direction corresponding to the maximum value selected by abovementioned means for selecting a direction is the direction of crest lines of the pattern of crest lines in the unit area. But a direction of crest lines cannot be always detected correctly in a center portion of a pattern of crest lines, in a background portion of a picture image, or in an unclear portion of a picture image. In such a case, the selected direction of crest lines in a unit area in the above-mentioned situations may be corrected by using a plurality of detected directions of crest lines of a pattern of crest lines in a plurality of unit areas surrounding the unit area, for a direction of the crest lines thereof to be detected.

The present invention will be described hereinafter in detail by way of examples with reference to the accompanying drawings.

BRIEF DESCRIPTION OF THE DRAWINGS

FIG. 1 is a schematic diagram of the apparatus for detecting a pattern of crest lines according to the present invention;

FIG. 2 shows a schematic construction of the apparatus using a microcomputer;

DESCRIPTION OF THE PREFERRED EMBODIMENTS

Figure 3A:
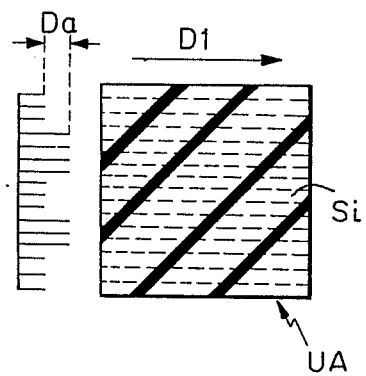
FIGS. 3a, 3b, 3c are views of a unit area for explaining the principle of the present invention.

FIG. 1 is a schematic diagram of the apparatus according to the present invention.

Referring to FIG. 2, a pattern of crest lines such as a dactylogram is displayed by a charge coupled device camera 10, the picture image of the pattern, which is divided into a plurality of picture elements (many picture elements) is transmitted to a picture image treatment apparatus 14 consisting of, for example, a microcomputer, through an analog-digital converter (A/D converter) 12. In more detail, each picture element of the picture image is input to a data memory 16 in turn through an I/O in the microcomputer 14 as shading information consisting of, for example, eight bits of information. The shading information may be one bit of information, as the most simple type of information. Namely, "0" of one bit of information is "White", and "1" of the same is "Black". A program described later for a treatment of the picture image is stored in a program memory 18.

Figure 4:
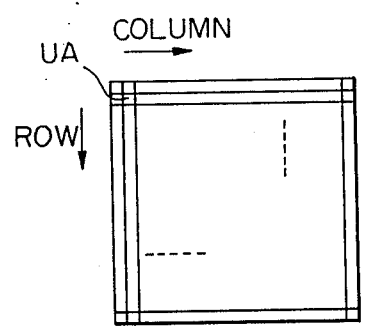
FIG. 4 shows a whole picture image area for detecting a pattern of crest lines, constructed by an assembly of a plurality of unit areas.

Considering a rectangular picture image region to be treated as shown in FIG. 4, the rectangular region consists of, for example, 512×512 picture elements, namely the region is divided into 512 sections in the column and row directions, respectively. A group of picture elements, for example, 16×16 picture elements adjacent to each other, is treated as a unit area hereinafter. A direction of crest lines of the picture image in each unit area is detected, and therefore, the directions in 32×32 unit areas are detected.

Figure 3B:
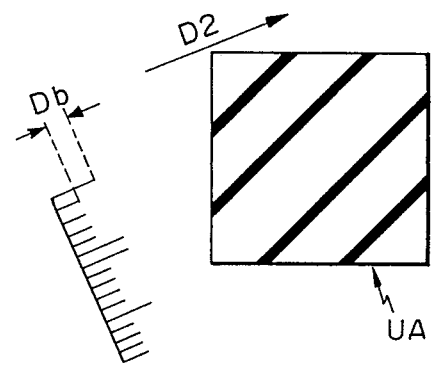
Figure 3C:
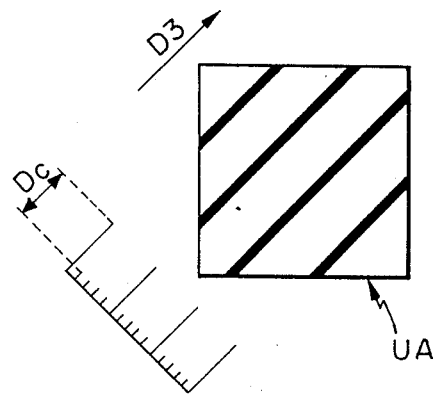
Figure 5:
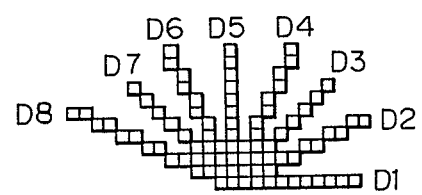
FIG. 5 shows eight series of picture elements in eight directions, as an example.

The principle of the operation of the present apparatus for detecting the pattern of crest lines in each unit area is described in more detail with reference to FIGS. 3a, 3b, and 3c. Each rectangular area in FIGS. 3a, 3b, and 3c is the same unit area UA. Sixteen series Si (i=1, 2, 16) of picture elements, each picture element being entrained in the column direction D1, are considered in FIG. 3a. Sixteen picture elements are entrained in each series Si of picture elements. Note, each series Si will be referred to as a slit Si hereinafter. The pattern of shading, white or black, is displayed in the unit area UA, showing a part of the pattern of the rest lines. Each mean value of the shading of sixteen picture elements in each slit Si is designated as a bar height of a bar graph at the left side of the unit area UA. As mentioned above, a mean value is used as an evaluated shading value, but another evaluated value, for example, an accumulated value of a shading of sixteen elements in each slit Si can be used as the evaluated shading value. A mean value is smaller than an accumulated value, and thus the mean value is preferred from the viewpoint of an effective utilization of a memory in a microcomputer. In FIGS. 3b and 3c, the mean values for other directions D2 or D3 shown in FIG. 5 are designated in the same manner as in FIG. 3a. Dc is the largest value among three values Da, Db, and Dc, each of which is the difference between the maximum and the minimum evaluated mean values for each direction D1, D2, or D3. This is based on the fact that the direction D3 corresponding to the largest value Dc shows the direction of crest lines of the pattern in the unit area UA. That is, the direction D3 having the value Dc is selected as a direction of crest lines in the unit area UA. The above-mentioned process is applied for each of the other unit areas. Before the process is applied for each unit area UA, the predetermined number of slit directions, for example, directions D1–D8 as shown in FIG. 5, are predetermined. Many directions should be preset in equi-spaced angular positions, in order to correctly detect a direction of crest lines, but this depends on the memory capacity of the picture image treatment apparatus 14 (FIG. 2) or the size of a picture element, etc.

Figure 6A:
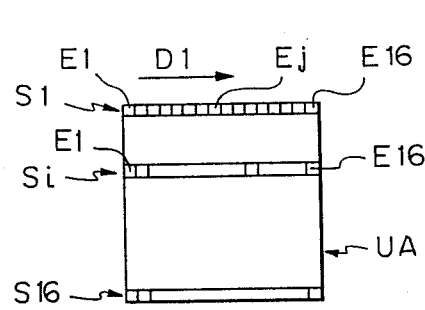
FIGS. 6a, 6b show a unit area which is one element of the picture image area shown in FIG. 4, shown by using one series of picture elements in one direction shown in FIG. 5.
Figure 6B:
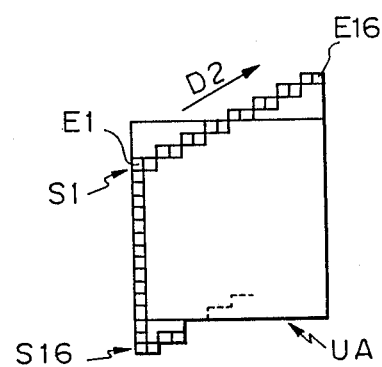

Each slit can be constructed by using picture elements in other unit areas adjacent to the unit area, as shown in FIG. 6b for the direction D2. The directions D1 and D5 of all directions shown in FIG. 5 can be constructed only by a series of picture elements in one unit area. The number of picture elements is short when the unit area in the periphery portion of the picture image to be treated shown in FIG. 4 is treated for one direction. As a special treatment for such a case, a predetermined shading value may be applied for the missing elements. Also, the peripheral unit areas need not be treated.

Figure 7:
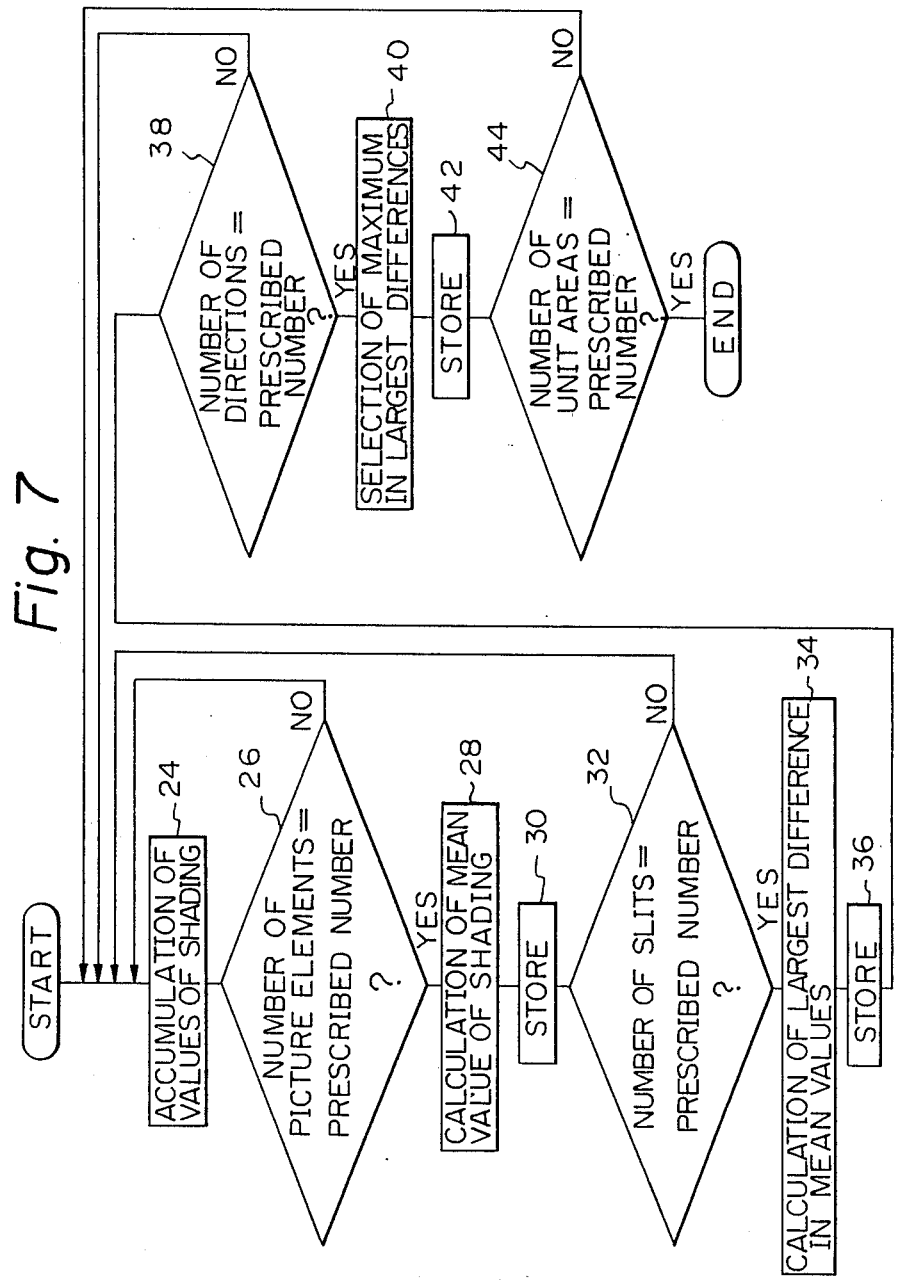
FIG. 7 is a flow chart of the operation of the apparatus.

Referring to FIG. 7, the flow of the treatment in the present apparatus for detecting the pattern of crest lines is explained for the case of the direction D1 shown in FIG. 6a, as an example. First, an individual shading value is accumulated for sixteen elements E1–E16 E16 in the first slit S1 at steps 24 and 26. That is, the "prescribed number" at step 26 is 16, which is equal to the number of picture elements Ej in one slit. After the accumulation, at step 28, the accumulated value is divided by 16 (equal to the number of picture elements) to calculate a mean shading value as an evaluated shading value, and then the mean value is stored in the data memory 16 shown in FIG. 2 at step 30. The "prescribed number" at step 32 is 16, which is equal to the number of slits in the unit area UA, and thus sixteen mean values are stored. Then, the largest difference in the sixteen mean values stored in the data memory 16 is calculated in step 34, and stored in the data memory 16 at step 36. The "prescribed number" at step 38 is 8, which is equal to the number of the directions D1–D8 in FIG. 5. The process of steps 24 to 36 is repeated for each direction in one unit area UA, i.e., is repeated eight times in one unit area. Then, the maximum is selected from the group of the eight largest differences, each of which corresponds to each direction D1, D2—, or D8, at step 40, and the specific direction corresponding to the maximum is stored in the data memory 16 at step 42.

The above-mentioned steps are repeated for each unit area at step 44. That is, the process is repeated 32×32 times in this embodiment. After the process, if necessary, each of the 32×32 directions stored in the data memory 16 can be drawn by a plotter through the I/O of the microcomputer 14, or can be output in another desired form.

Figure 8:
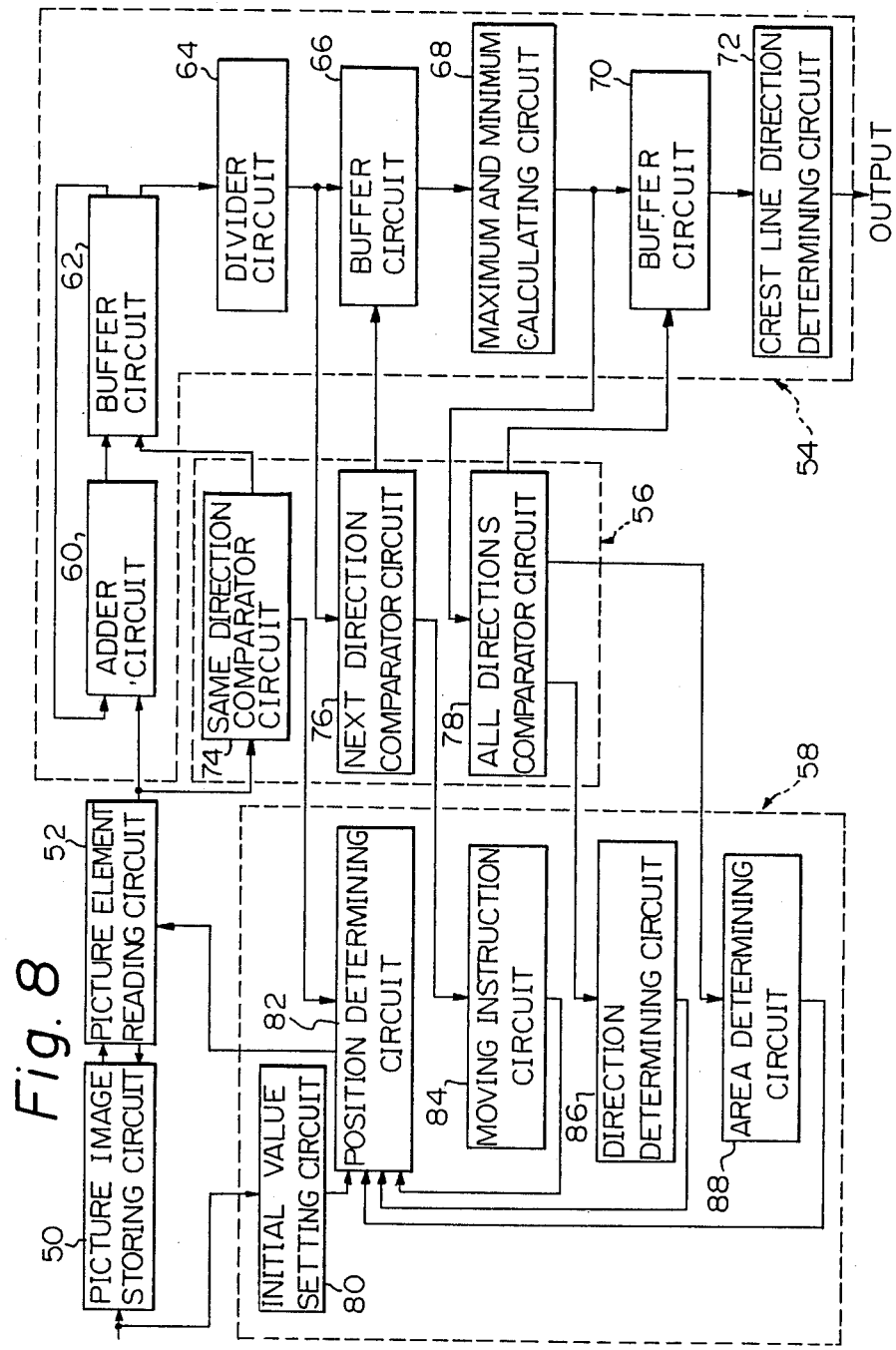
FIG. 8 shows another example of the apparatus according to the present invention.

FIG. 8 shows another embodiment of the present apparatus for detecting a pattern of crest lines. A picture image of a dactylogram, or the like is stored in the picture image storing circuit 50, through a not shown CCD camera or A/D converter, as, for example, 512×512 picture elements, each of which corresponds to a shading value. In the calculation portion 54, the shading values of picture elements read by the picture element reading circuit 52 from the picture image storing circuit 50 are added, and the direction of the crest lines is detected. In the comparator portion 56, the number of picture elements read from the picture image storing circuit 50 is counted, and the summed result is transferred to the buffer circuit in the calculation portion 54 when the counted number reaches a predetermined number. When the counted number is lower than the predetermined number, a signal is output to a picture element position determining portion 58. In the portion 58, the position of a picture element to be read by the circuit 52 from the picture image storing circuit 50, to which a picture image is input, is determined, and the determined position of the picture element is input to the picture element reading circuit 52. Accordingly, the picture elements are read from the picture image storing circuit 50, and the shading values of the picture elements are sent to the calculation portion 54.

The process for determining the direction of crest lines is now described in detail. When a picture image is input to the picture image storing portion 50, a signal indicating that the picture image has been input to the portion 50 is input to the initial value setting circuit 80. This process is explained with reference to FIGS. 4, 5, 6a, and 6b, and starts from the unit area at the position (column No., row No.)=(1, 1). The position information in the position determining circuit 82 is initialized by the initial value setting circuit 80. Namely, the position data of the unit area UA (1, 1), the direction D1, the slit S1, and the picture element E1 are set and are sent to the picture element reading circuit 52. Then, the shading value corresponding to the picture element E1 is read from the circuit 50 to be input to the adder circuit 60, and at the same time, counted by the same direction comparator circuit 74.

The shading information of the picture element E1 input to the adder circuit 60 is temporarily stored in the buffer circuit 62. In this embodiment, the number of picture elements in one slit is 16. The number counted by the same direction comparator circuit 74 is 1, and thus signal that the counted number is less than 16 is sent to the position determining circuit 82. Then the circuit 82 outputs a signal to read a shading value of the next picture element E2 to the picture element reading circuit 52 and, the shading value of the picture element E2 is added to that of the picture element E1 stored temporarily in the buffer circuit 62, and temporarily, re-stored in the buffer circuit 62, and the number counted by the circuit 74 becomes 2. When the above-mentioned process is repeated until the addition of the shading value of the picture element E16 is completed, the counted number in the circuit 74 is 16, and the accumulated shading value of the picture elements from E1 to E16 stored in the buffer circuit 62 is sent to the divider circuit 64 in response to a signal indicating that the counted number in the circuit 74 is 16, and the value in the buffer circuit 62 is then cleared. The accumulated value is divided by 16 in the divider circuit 64 to obtain a mean value, and this mean value is stored in the buffer circuit 66.

At the same time as the mean value is stored in the circuit 66, a signal is input to the next direction comparator circuit 76, and the counted number in the circuit 76 is set to 1. The circuit 76 sends a signal to the moving instruction circuit 84 to send a signal to the position determining circuit 82 indicating that the position of the slit to be selected has been changed from S1 to S2, and the position information is set to the unit area (1, 1), the direction D1, the slit S2, and the picture element E1. Then, the mean shading value of sixteen picture elements E1–E16 in the slit S2 is stored in the buffer circuit 66, after repeating the same process as above-mentioned. In the same manner, the process is repeated up to slit S16, so that the counted number in the next direction comparator circuit 76 becomes 16, and sixteen mean shading values, each of which corresponds to each of the sixteen slits S1–S16, are sent to the maximum and minimum calculating circuit 68 to determine the maximum value and the minimum value. The difference between the maximum value and the minimum one is stored in the buffer circuit 70.

A signal is also sent to the all directions comparator circuit 78, so that the counted number in the circuit 78 is set to 1, and a signal is input to the direction determining circuit 86, and thus a signal indicating that the same process as for the direction D1 is to be adapted for the direction D2 is sent to the position determining circuit 82. Accordingly, the position information is set to the unit area (1, 1), the direction D2, the slit S1, and the picture element E1, as shown in FIG. 6b. The same process as for the direction D1 is adapted for the direction D2, and the largest difference in a group of mean shading values, each of which values corresponds to each slit S1, ..., or S16 for the direction D2, is stored in the buffer circuit 70. When the process is completed for the directions from D1 to D8, the counted number in the all directions comparator circuit 78 is set to 8, and the shading information of the eight largest differences for the eight directions D1–D8 stored in the buffer circuit 70 is sent to the crest line direction determining circuit 72. In the circuit 72, the maximum value is selected from among the eight largest differences, and the direction corresponding to the maximum value is determined as the crest line in the unit area (1, 1) by the circuit 72. The counted number in the circuit 78 is then cleared and a signal is sent to the area determining circuit 88, which outputs a signal indicating that the next unit area is to be treated by the position determining circuit 82. Accordingly, the position information is set to be the unit area (1, 2), the direction D1, the slit S1, and the picture element E1, and the same process as for the unit area (1, 1) is repeated for all unit areas.

In the above-mentioned two embodiments, a unit area is constructed by 16×16 picture elements, but may be constructed in another form, for example, 16×8 picture elements.

As apparent from the foregoing description, the present invention provides the apparatus for detecting the pattern of crest lines, which apparatus can detect the direction of crest lines by a simple calculation consisting of addition, subtraction, multiplication, and division, or by a comparison of two values (a comparison corresponding to an addition or a subtraction), using evaluated shading values in slits for each direction of every gathered region of a plurality of picture elements, which elements are obtained by a mechanical division of the object region to be treated, and can correctly detect the direction of crest lines even when the crest line is cut off, crushed, or branched off, on the way thereof, and is simple.

We claim:

1. An apparatus for detecting a pattern of crest lines, which pattern is divided into a plurality of picture elements on a picture image thereof, each picture element having a shading value, each shading value being one of a predetermined number of values, comprising:
    means for storing said each shading value in correspondence to each picture element having said shading value, in order;
    means for calculating a first group of evaluated values for each direction of a plurality of predetermined directions in a unit area consisting of a group of said picture elements, each of which is adjacent to one another, each of said first group of evaluated values being an evaluated shading value in each series of picture elements along one direction of said plurality of predetermined directions;
    means for selecting a second group of values, each of which value is a largest difference in said first group of evaluated values for each direction; and
    means for selecting a direction corresponding to a maximum value in said second group of values,
    thereby determining a direction of crest lines of a pattern of crest lines in said unit area.

2. An apparatus for detecting a pattern of crest lines according to claim 1, wherein said predetermined number of shading values is two, one shading value corresponding to "White" and another corresponding to "Black".

3. An apparatus for detecting a pattern of crest lines according to claim 1, wherein each of said predetermined directions is equispaced in angular position.

4. An apparatus for detecting a pattern of crest lines according to claim 2, wherein each of said predetermined directions is equispaced in angular position.

* * * * *